United States Patent [19]

Davis et al.

[11] Patent Number: 5,316,925
[45] Date of Patent: May 31, 1994

[54] T-CELL RECEPTOR SPECIFIC FOR ANTIGEN POLYPEPTIDES AND RELATED POLYNUCLEOTIDES

[76] Inventors: Mark M. Davis, 422 Foxborough Dr., Mountain View, Calif. 94041; Stephen M. Hedrick, 1031 Santa Queta, Solana Beach, Calif. 92075

[21] Appl. No.: 924,395

[22] Filed: Dec. 3, 1992

Related U.S. Application Data

[63] Continuation of Ser. No. 663,809, Oct. 22, 1984, abandoned, which is a continuation-in-part of Ser. No. 585,333, Mar. 1, 1984, abandoned.

[51] Int. Cl.$^5$ .................. C07H 15/12; C12P 19/34; C12N 5/16; C12N 15/12
[52] U.S. Cl. .................. 435/91.2; 435/254.11; 435/252.3; 435/252.33; 435/320.1; 435/172.3; 435/240.2; 435/91.51; 435/6; 435/91.5; 536/23.1; 536/23.5; 536/24.31; 536/25.4; 935/9; 935/19; 935/20; 935/21; 935/70; 935/68; 935/71; 935/72; 935/73; 935/4
[58] Field of Search .................. 536/27, 23.1, 23.5, 536/23.53, 24.31; 435/91, 320.1, 172.3, 240.2, 252.3, 69.1, 69.3; 935/4, 6, 9, 11, 22, 29, 78, 80, 66, 70, 72

[56] References Cited

U.S. PATENT DOCUMENTS

| | | | |
|---|---|---|---|
| 4,356,270 | 10/1982 | Itakura | 435/320.1 |
| 4,363,877 | 12/1982 | Goodman et al. | 435/320.1 |
| 4,394,443 | 7/1983 | Weissman et al. | 435/6 |
| 4,446,235 | 5/1984 | Seeburg | 435/91 |
| 4,468,464 | 8/1984 | Cohen et al. | 435/320.1 |
| 4,713,332 | 12/1987 | Mak | 435/69.1 |

OTHER PUBLICATIONS

Kronenberg et al., J. Exp Med. 152: 1745–1761 (1980).
Hamilton, Science 250: 1331–1332 (1990).
Science Citation Index Five-Year Cumulation Guide and Lists of Source Publications (p. 47).
Lewin, R. 1987. Science, 237, 1570.
Creighton, T. E. 1983, in: *Proteins: Structures and Molecular Principles.* W. H. Freeman and Co., New York, pp. 93–99.
Baker, J. J. W. et al. 1982. in: *Fourth Edition. The Study of Biology.* Addison–Wesley Publ. Co., Reading, Mass. p. 922.
McIntyre et al. 1983 Cell. 34, 739–746.
Kappler et al. 1983. Cell. 34, 727–737.
Marx, J. L. 1983 Science. 221, 1278.
Berzofsky, J. 1983. Immunol. Today, 4, 299–301.
Marx, "Likely T Cell Receptor Gene Cloned" Science 221 pp. 1278–1279 (Sep. 1983).
Berzofsky, "T–Cell Activation by Antigen: Promising Clues to Reception Genes and Molecules" Immunology Today 4 pp. 299–301 (1983).
Yanagi et al, "A Human T Cell Specific cDNA Clone Encodes a Protein having Extensive Homology to Immunoglobulin Chains" Nature 308 p. 145 (1984) C. A. 100:204488h.
Hedrick et al. "The Isolation of cDNA Clones Encoding T Cell Specific Membrane Associated Proteins" Nature 308 p. 149–153 (1984) C. A. 100:151950u.

(List continued on next page.)

*Primary Examiner*—Christopher S. F. Low

[57] ABSTRACT

Oligonucleotide sequences are provided coding for T-cell-specific antigen receptors or fragments thereof. The oligonucleotide sequences can be used as probes for detecting helper and cytotoxic T-cells, preparing and isolating DNA sequences encoding for the receptor polypeptide, and in constructions for expression of receptor polypeptides or fragments thereof. In addition, processing signals from the receptor subunits can be employed in conjunction with modified wild type oligonucleotide sequences or non-wild type oligonucleotide sequences.

TM86 was deposited at the A.T.C.C. on Mar. 1, 1984 and given Accession No. 40099. TT11 was deposited at the A.T.C.C. on Oct. 22, 1984 and given Accession No. 40141.

47 Claims, 5 Drawing Sheets

OTHER PUBLICATIONS

Kronenberg et al. "Helper and Killer T Cells do not Express B Cell Innumoglobulin Joining and Constant Region Genes" Journal of Experimental Medicine 152 pp. 1745≅1761 (1980).

Kronenberg et al, "Three T Cell Hybridomas do not Contain Detectable Heavy Chain Variable Gene Transcripts" Journal of Experimental Medicine 158 pp. 210-227 (1983).

Allison et al, "Tumor Specific Antigen of Muring T-Lymphoma Defined With Monocolonal Antibody" Journal of Immunology 129(5) pp. 2293-2300 (1982).

Acuto et al. "The Human T Cell Receptor: Appearance in Ontogeny and Biochemical Relationship of and Subunits on IL-2 . . . " Cell 34 pp. 717-726 (1983).

Meuer et al, "Evidence for the T3-Associated 90K Heterodimer as the T-Cell Antigen Receptor" Nature 303 pp. 808-810 (1983).

Kappler et al, "The Mouse T Cell Receptor: Comparison of MHC-Restricted Receptors on Two T-Cell Hybridomas" Cell 34 pp. 727-737 (1983).

FIG. 2

```
                  ———— 5' UT ————|———— LEADER PEPTIDE ————|———— VARIABLE REGION ————
                                                 10                          20                          30
                                    M  S  C  R  L  L  L  Y  V  S  L  C  L  V  E  T  A  L  M  H  N  T  K  I  T  Q  S  P  R  Y  L
  CCGTCTGGAGCCTGATTCCACC ATG AGC TGC AGG CTT CTC TAT GTT TCC CTC TGT CTT GTG GAA ACA GCA CTC ATG AAC ATT ACT AAA ATT ACT CAG TCA CCA AGA TAT CTA   86T1

V  Y  I  S  *  *  F  I
                                           AG GTT TAC ATT TCT GTT TAA TAG TTC ATC   86T3

CHO                40
    I  L  G  R  A  N  K  S     L  E (C) E  Q  H  L  G  H  N  A  N  Y  V  Y  K  Q  S  A  E  K  P                50             P  P  E  L  H  F  L  Y  N  L  K
  ATC TTG GGA AGA GCA AAT AAG TCT TTG GAA TGT GAA CAA CAT CTG GGA CAT AAT GCT ATG TAC GTG TAT AAA CAG AGC GCT GAG AAG CCG CCA GAG CTC ATG TTT CTC TAC AAT CTT AAA   86T1

K  S  L  V  P  L  L  P  L  Q  A  G  Y  K  L  I  L  I  N  S  H  L  L  K  K  S  A  V  L (C) E  T  R  I  H  *  K  K  S  T
  AAG AGT TTA GTG CCT CTA TTA CCT CTA CAA GCT GGT TAC AAA TTA ATT TTA ATT AAC TCC CAC TTA TTA AAA AAA TCT GCA GTT CTT TGT GAG ACA CGT ATT CAT TAA AAA AAA TCA ACA   86T3

CHO              80                                                          90                                         100
    Q  L  I  R  N  E  T     V  P  S  R  F  I  P  E (C) P  D  S  S  K  L  L  L  H  I  S  A  V  D  P  E  D  S  A  V  Y  F (C) A             110
  CAG TTG ATT CGA AAT GAG ACG GTG CCC AGT CGT TTT ATA CCT GAA TGC CCA GAC AGC TCC AAG CTA CTT TTA CAT ATA TCT GCC GTG GAT CCA GAA GAC TCA GCT GTC TAT TTT TGT GCC   86T1

*  V  K  G  K  I  K  T  H  H  T  K  N  K  H (C) K  F  F  D  T  Y  N  Y  T (C) T  H  I  R  N  F  P  I  Y  V  T  I  F            
  TAA GTA AAA GGC AAA ATT AAG ACA CAC CAC ACC AAA AAT AAG CAC TGT AAA TTT TTT GAT ACG TAT AAT TAT ACA TGT ACA CAC ATA ATT AGG AAT TTT CCT ATC TAT GTG ACC ATT TTC   86T3

R  G  A  A  Y  L  V  S  S  S  P  Q  G  V  D  L  W [E] G  P [F  L  Y] K  A
  AGA GGA GCA GCT TAT CTG GTG TCT TCC AGC CCT CAA GGG GTA GAC CTA TGG GAG GGT CCC TTT TTG TAT AAA GCT   86T5

G  T (C) G  E [E] T [F  L  Y] H  D
  A GGC ACC TGT GGG GAA GAA ACT TTT TTG TAT CAC GAT   TM86
```

```
                                    ──────────── CONSTANT REGION ────────────▶
                                                             130
                 110                         120                    S  Q  D
       L  S  V  K  P  N  I  Q  N  P  E  P  A  V  Y  Q  L  K  D  P  R  S  Q  D
I  F  G  T  L  L
ATC TTT GGA ACT GGC ACT CTG CTT TCT GTC AAG CCA AAC ATC CAG AAC CCA GAA CCT GCT GTG TAC CAG TTA AAA GAT CCT CGG TCT CAG GAC 160
           140                           150                         T  D  K  T  V  L
S  T  L  ©  L  F  T  D  F  D  S  Q  I  N  V  P  K  T  M  E  S  G  T  F  I  T  D  K  T  V  L
AGC ACC CTC TGC CTG TTC ACC GAC TTT GAC TCC CAA ATC AAT GTG CCG AAA ACC ATG GAA TCT GGA ACG TTC ATC ACT GAC AAA ACT GTG CTG

CHO                            190
                 170                          ┌─ N  Q  T ─┐  S  F  T  ©  Q  D  I  F  K  E  T  ┌─ N
D  M  K  A  M  D  S  K  S  N  G  A  I  A  W  S  N  Q  T  S  F  T  Q  D  I  F  K  E  T  N
GAC ATG AAA GCT ATG GAT TCC AAG AGC AAT GGG GCC ATT GCC TGG AGC AAC CAG ACA AGC TTC ACC TGC CAA GAT ATC TTC AAA GAG ACC AAC

CHO                                                220
      ┌─ T ─┐                                                    ┌─ N  L  S ─┐
A  T  Y  P  S  S  D  V  P  ©  D  A  T  L  T  E  K  S  F  E  T  D  M  N  L  N  F  Q  N  L  S
GCC ACC TAC CCC AGT TCA GAC GTT CCC TGT GAT GCC ACG TTG ACC GAG AAA AGC TTT GAA ACA GAT ATG AAC CTA AAC TTT CAA AAC CTG TCA

TRANSMEMBRANE                                        CYTOPLASMIC
                       230                         240                      250
V  M  G  L  R  I  L  L  L  K  V  A  G  F  N  L  L  M  T  L  R  L  W  S  S  ***
GTT ATG GGA CTC CGA ATC CTC CTG CTG AAA GTA GCG GGA TTT AAC CTG CTC ATG ACG CTG AGG CTG TGG TCC AGT TGA GGTCTGCAAGACTGACAGA

GCCTGACTCCAAGTTCCGTCTCCTCTTCACCCCTCCGCTCCCTCTTCAAGGCAAAAGGAGCCGGCGTGTCTGGGGTCTGGCCCTGATTCACAATCCCACCTAGATCCCCAGATTGTGAG

GAAGGTTGCTAGAGAGCTAAGCGC
```

FIG. 3B (Cont.)

T-CELL RECEPTOR SPECIFIC FOR ANTIGEN POLYPEPTIDES AND RELATED POLYNUCLEOTIDES

This invention was supported in-part by Grant No. AI19512 from the National Institutes of Health.

This is a continuation of application Ser. No. 06/663,809, filed Oct. 22, 1984, now abandoned, which is a continuation in part of application Ser. No. 06/585,333 filed Mar. 1, 1984, now abandoned.

BACKGROUND OF THE INVENTION

1. Field of the Invention

The hematopoietic system is extraordinarily complex, which is not surprising in view of the central role blood cells play in the maintenance and survival of the host. One aspect of great importance is the manner in which the host protects itself from various pathogens. Two families of cells play a salient role in protecting the host, B-cells and T-cells. The mystery of how the B-cells are able to produce an extraordinary variety of immunoglobulins has been explained to a substantial degree. The germline DNA is now known to undergo rearrangements, so as to join various exons together to produce a variable region which is then joined to differing constant regions as the B-cell matures. The mechanism by which the DNA undergoes the rearrangement and the subsequent transcript is spliced to produce a messenger RNA coding for a specific immunoglobulin has been an exciting adventure demonstrating the potency of the tools afforded by the developments in molecular biology. Another class of cells important to the immune system of the host is the T-cells. These cells differ from the B-cells in that they do not secrete immunoglobulins, although they appear to have a similar range of antigenic specificities. Particularly, helper T-cells, which are involved in stimulating B-cell proliferation, can have specificity analogous to that of B-cells, with the additional requirement that they must also recognize self-major histocompatability determinants simultaneously.

The specificity of T-cells can find application in a wide variety of situations. If one could modify a helper T-cell by introducing a foreign receptor site, one could change the response of the host to a foreign antigen. Furthermore, in many situations, it may be of interest to determine whether a cell is a helper T-cell or other type of cell. In addition, one has the opportunity to determine monoclonality in the host, which can be useful in the diagnosis of T-cell leukemias. Also, having DNA sequences which encode for portions of the T-cell antigen-specific receptor would allow for constructions involving the combination of native T-cell sequences with foreign sequences to produce novel proteins which could act as receptors. Also, antisera and monoclonal antibodies could be generated against specific parts of the protein, using either synthetic peptides or producing the protein in an expression vector. By employing hybridization with DNA sequences, subsets of T-cells may be determined as well as genetic differences and defects.

2. Description of the Prior Art

The second domain of HLA-DC has been shown to be homologous to immunoglobulin. Auffray et al., *Proc. Natl. Acad. Sci. USA* (1982) 79:6337-6341. The sequence about the intrachain disulfide bond in the immunoglobulin variable region is discussed by Kabat et al., in *Sequences of Immunological Interest*, U.S. Dept. of Health and Human Services, Washington, D.C. (1983). Cross-reactivity between B-cell anti-idiotypic antisera and T-cells is reported by Eichmann and Rajewsky, *Eur. J. Immunol.* (1975) 5:661-666; Binz and Wigzell, *J. Exp. Med.* (1975) 142:197-211, and Augustin et al., in *Regulatory T Lymphocyte* (eds. Pernis and Vogel) 171-184, Academic Press, N.Y., 1980. Lack of nucleotide sequence similarity between T-cell specific genes and immunoglobulin coding genes is reported by Kronenberg et al., *J. Exp. Med.* (1980) 152:1745-1761 and Kronenberg et al., ibid. (1983) 158:210-227, among others. Murine T-cell specific proteins are reported by Kappler et al., *Cell* (1983) 34:727-737 and McIntyre and Allison, ibid. (1983) 34:739-746. Allison et al., *J. Immunol.* (1982) 129:2293-2300; Haskins et al., *J. Exp. Med.* (1983) 157:1149-1169; Meuer et al., *Nature* (1983) 303:808-810 and Samuelson et al., *Proc. Natl. Acad. Sci. USA* (1983) 801:6972-6976 report the immunoprecipitation from T-cells of a disulfide linked heterodimer composed of two distinct glycoproteins of 37-50 kd in size. McIntyre and Allison, supra (1983) and Acuto et al., *Cell* (1983) 34:717-726 report that the heterodimer appears to have variable and constant portions by peptide map analyses. Heber-Katz et al., *J. Exp. Med.* (1982) 155:1086-1099 and Hedrick et al., *Cell* (1982) 30:141-152 report the production of MHC-restricted T-helper hybridomas, which disclosure is incorporated herein by reference. Davis et al., in *B and T Cell Tumors*, UCLA Symposium Vol. 24 (eds. Vitteta and Fox) 215-220, Academic Press, N.Y. 1982, report that T and B lymphocytes differ by a very small fraction of their gene expression.

Saito, *Nature* (1984) 309:757-762, reports a T-cell-specific cDNA clone which is rearranged in cytotoxic T-cell DNAs and has variable, constant and joining region homologous elements. Siu et al., *Cell* (1984) 37:393-401 and Kavaler et al., *Nature* (1984) 310 421-423, report the presence of diversity elements in the β-chain. The α-chain of T-cell receptor molecules has been reported to be as diverse as the β-chain (Kappler et al., *Cell* (1983) 35:295-302).

SUMMARY OF THE INVENTION

A technique is provided whereby rare messenger RNA is isolated. By means of this technique, DNA sequences encoding for antigen-specific receptors in T-cells are obtained as well as other T-cell specific gene products. The DNA can be used in a variety of ways, such as nucleotide probes, combining with foreign DNA sequences to produce novel T-cell receptors, which can be used in an analogous manner as antibodies, or constructs can be provided which provide for extrachromosomal elements or integration into a host genome, where the hybrid proteins may be expressed and transported to the membrane.

BRIEF DESCRIPTION OF THE DRAWINGS

FIG. 2 shows the complete nucleotide sequence of 86T1 and partial sequences of the other cDNA clones, indicating the 5'-untranslated region (UT), the leader polypeptide, variable, joining, and constant regions, with the numbering following the amino acid sequence of 86T1 and possible carbohydrate attachment sites (CHO)(N-X-S or N-X-T) noted.

DESCRIPTION OF THE SPECIFIC EMBODIMENTS

Figure 1:
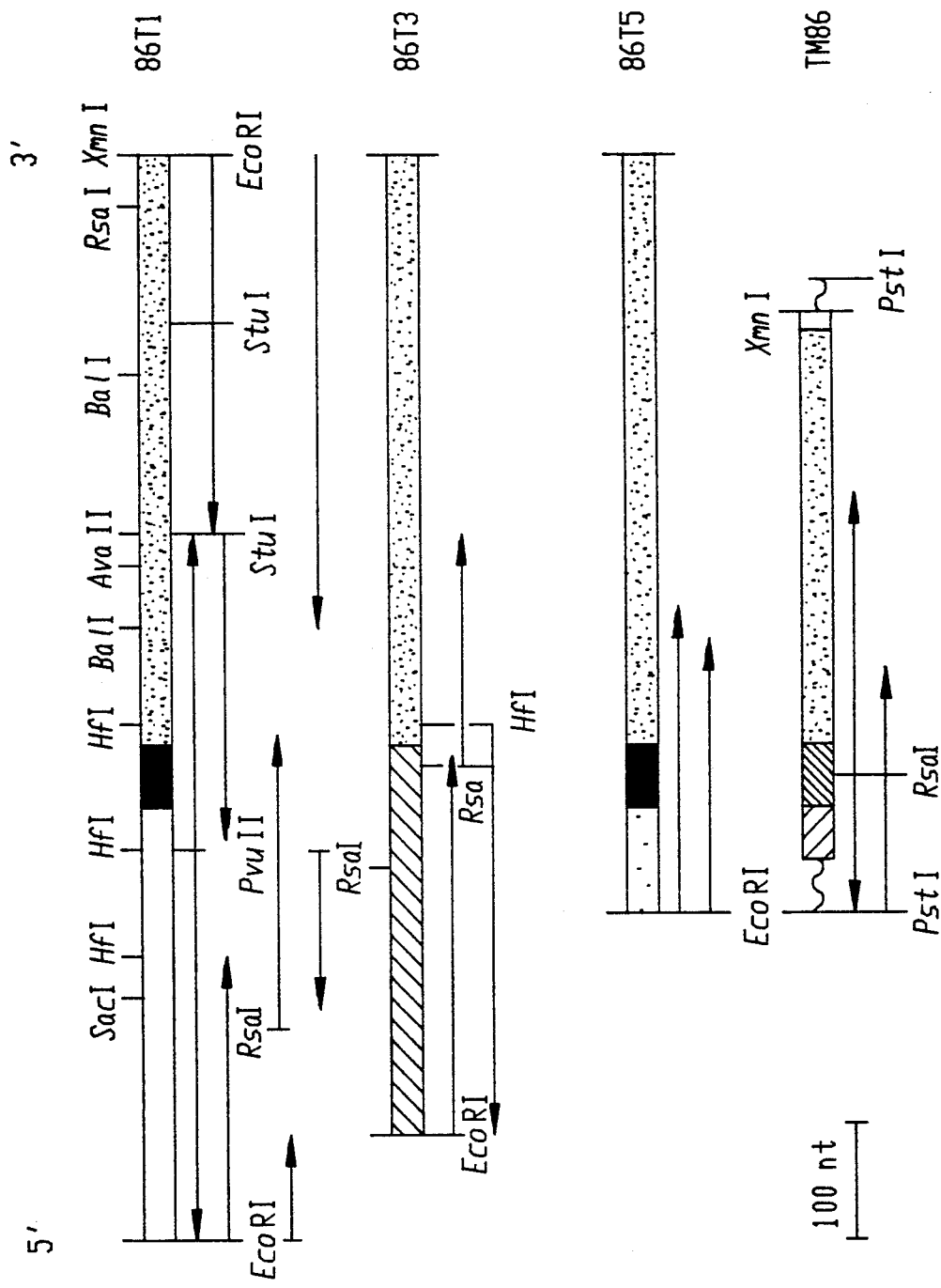
FIG. 1 is a restriction map of T-cell antigen receptor fragments, where shaded areas indicate major homologies between the different cDNA clones. Sequencing was by the procedure of Maxam and Gilbert, *Proc. Natl. Acad. Sci. USA* (1977) 74:560, with thick arrows representing 3'-end labeling (Klenow) and the arrows 5'-end labeling (polynucleotide kinase).

In accordance with the subject invention, novel DNA sequences are provided involving in-whole or in-part coding sequences for antigen-specific T-cell receptors or fragments thereof, specifically involving functional regions, which may be found on one or more exons in the germline and rearranged DNA or in-whole or in-part as cDNA from a mature messenger RNA.

The mammalian T-cell receptors appear to be 80–90 kdal heterodimers, which are disulfide linked, and composed of two distinct glycoproteins of about 40 to 50 kd (kilodaltons), referred to as the α- and β-subunits. The two glycoproteins have variable and constant regions or domains by peptide map analysis.

The DNA sequences encoding for the glycoproteins of the heterodimer are divisible into variable, joining and constant regions, analogous to immunoglobulins, as evidenced by the sequences having significant homology with the immunoglobulin sequences and by the independent assortment of the J-like elements. Each of the subunits appears to have diversity (D) regions comparable to the heavy chain of immunoglobulins.

The α- and β-subunits have many similarities between themselves, other T-cell membrane proteins and immunoglobulins or B-cell receptor proteins. For the most part, the overall homology is low with few similarities of either amino acid sequence or nucleotide sequence in the constant regions. (The methionine of the leader peptide will be used as 1 for the amino acid sequence.) The cysteine spacing is found to be between about 65 to 70 amino acids in the variable region (α-65; β-69; Igλ or κ-65). In addition the sequence "WYRQ" in the variable region of the α-chain at about residue 55 finds analogy in the β-chain in "WYKQ" and analogous sequences at comparable positions in immunoglobulins. In the variable regions, the sequence "DSA-Y-CAV" is found in the region of residues of about 100–115, with one or two differences in amino acids.

The J region appears to be the most highly conserved with 7 of 16 residues of the α-chain the same as the β-chain and significant homology with consensus sequences of murine heavy and light chains.

Also characteristic of the T-cell receptor sequences is the sequence "ILLXK" where X is L or G, having a basic amino acid in the transmembrane region.

In support of a D or diversity region, 5' to the "SGN" sequence at about residues 115 to 120, is the nucleotide sequence "$G_5$". In 7 of 14 β-chain putative D regions, runs of "$G_{3-7}$" are found on the 3'-side, which finds analogy in immunoglobulin heavy chain D regions.

The α- and β-chains are encoded in germline DNA which is subject to rearrangement to provide a transcript which may be further processed. Either the genomic DNA may be used or cDNA from the mature transcript for purposes described hereinafter.

Each of the chains has from 3 to 5, usually 4 to 5 N-glycosylation sites, where some or all of them may be employed.

The two chains of the heterodimer are different and appear to be derived from different gene loci. The sequences for a β-chain and an α-chain are set forth in FIGS. 2 and 3B, respectively. The chains may be divided up into regions associated with specific exons by analogy to immunoglobulins. The primary regions are the leader region, variable region (V), diversity region (D), which may be part of V, the joining region (J), the constant region (C), the transmembrane region (TM) and the cytoplasmic region (Cy).

The α-chain without glycosylation will be about 25 to 30 kD (kilodaltons), while the β-chain will be about the same or larger, being about 25 to 35 kD. With glycosylation the subunits will be about 35 to 50 kD each, usually 40 to 50 kD each, providing a sulfhydryl linked heterodimer of 80 to 90 kD.

For each of the subunits, the rearranged DNA in helper T-cells, including introns will generally be approximately 6 to 8 kbp, with individual exons being substantially smaller and approximating the size of cDNA sequences for domains plus whatever flanking regions are included.

The DNA sequence coding for the constant region (including the transmembrane and cytoplasmic region) will generally be about 400 to 600 nt (nucleotides), plus about 300 nt of 3' untranslated regions. These sequences will be characterized by having codons encoding for intrachain disulfide linkages between cysteines spaced apart about 100 to 200 nt, usually about 100 to 150 nt.

In conjunction with the constant region is a probable transmembrane sequence, primarily including hydrophobic amino acids and having from about 45 to 105 nt. This sequence will define the 3'-terminus of the constant region and may include about 5 to 15 codons (15 to 45 nt) for amino acids which extend into the cytoplasm of the cell.

The next region or domain which appears to have functional significance is the region analogous to the J region of immunoglobulins. As is known with immunoglobulins, there are a plurality of J regions, adjacent to a given C region ranging about 1 to 6 in number, more usually about 4 to 5. The J regions encode about 15 to 20 amino acids, the β-chain with 16 amino acids having greater similarity to the immunoglobulin heavy chain J regions, in that the heavy chain J regions are typically 17 amino acids, while the light chain J regions are typically 13 amino acids.

The J regions can be used in conjunction with constant regions which may or may not include the transmembrane sequence and cytoplasmic sequence to be joined to other DNA sequences, e.g., non-wild sequences, to produce hybrid sequences to allow for novel hybrid proteins on T-cell surfaces. (By "non-wild" is intended a sequence other than the wild-type or native sequence, while "foreign" intends from a source which does not normally exchange genetic information with the source of the T-cell antigen receptor DNA sequence.)

In order to have the hybrid proteins transported to the surface, the secretory leader sequence present with the T-cell antigen receptor is employed as the 5'-terminus. The sequence is of about 15 to 25 amino acids, more usually 18 to 24 amino acids. Thus constructs can be prepared, where various domains of the T-cell antigen receptor DNA sequence, which may include noncoding flanking regions, are separated by non-wild type DNA.

Novel DNA constructions can be employed for cloning and/or expressing the T-cell antigen receptor, individual subunits, fragments thereof, or combinations of fragments with non-wild DNA, including foreign DNA, to produce hybrid proteins. The fragments will be of at least about 15 nt, usually at least about 50 nt. These constructions will for the most part have the following formula:

$$(RS)_a—(M)_b—(tis)—(eis)—(T—AgR)—(ets)—(tts)$$

wherein:

"RS" indicates a replication system which may be derived from prokaryotes or eukaryotes, plasmids, phage, or viruses, where one or more replication systems may be involved which allow for replication in different hosts, e.g., unicellular microorganisms, and maintenance as extrachromosomal elements; illustrative replication systems or vectors include lambda, simian virus, papilloma virus, adenovirus, yeast 2 mμ plasmid, ColEI, pRK290, pBR322, pUC6, or the like, where the replication system may be complete or may be only a partial replication system, interacting with a helper plasmid or one or more genes present in the genome, e.g., COS cells; for cloning, a replication system will be employed, such as a plasmid or viral replication system recognized by the unicellular host, for example, bacteria, yeast, etc., particularly E. coli;

"a" is an integer of from 0 to 3, usually 1 to 3, being 0 where integration into the chromosome is desired, although integration can be achieved with native or foreign replication systems;

"M" intends a structural gene or cistron, referred to as a marker, with its transcriptional and translational regulatory signals which provides means for selecting host cells which contain the construct; markers include biocide resistance, such as resistance to antibiotics, e.g., ampicillin, chloramphenicol, neomycin, G418, or the like, toxins, heavy metals, etc.; immunity; complementation providing prototrophy to an auxotrophic host, or the like;

"b" is an integer of from 0 to 3, more usually 0 to 2, preferably 1 to 2;

"tis" intends the transcriptional initiation sequences for regulating transcriptional initiation and includes one or more promoters, including the native promoter by itself or in combination with other promoters, e.g., viral promoters or foreign promoters, as well as sequences which affect the promoter, such as operators, activators, enhancers, capping sequence, TATA and CAAT sequences, or the like, where the sequences will be organized in the construct so as to be able to fulfill their function;

"eis" intends the expression initiation sequences for regulating expression and includes any ribosomal binding site, the initiation codon as appropriate, oligonucleotides separating the ribosomal binding site and initiation codon, where such sequences affect expression, and the like;

"T-AgR" intends the T-cell antigen receptor or a hybrid DNA sequence comprising fragments of the T-cell antigen receptor and hybrid DNA sequences, where the sequences together provide for an open reading frame coding for the antigen receptor or hybrid protein;

"ets" intends expression termination sequences, which may include one or more stop codons and such other sequences as may be appropriate; and "tts" intends transcriptional termination sequences, which may include the transcriptional terminator, normally balanced with the transcriptional promoter and may be one or more terminators in combination with one or more stop codons, polyadenylation signal sequence, or the like.

The T-cell antigen receptor subunit or hybrid T-cell antigen receptor will for the most part have the following formula:

$$(S.L.)_c—(V—seq)—J—C—(TM)_d—(Cy)_e$$

wherein:

"S.L." intends a secretory leader sequence, which will encode for about 15 to 25 amino acids, more usually about 17 to 24 amino acids, and preferably about 19 to 23 amino acids having 45 to 75 nt, usually 51 to 72 nt, preferably 57 to 69 nt;

"c" is 0 or 1;

"V-seq" intends a DNA sequence which encodes for the variable region of the T-cell antigen receptor subunit or may be replaced by a sequence encoding for a different polypeptide, which DNA sequence will be in reading frame with the secretory leader sequence (S.L.) as appropriate or may have its own initiation codon in the absence of the secretory leader sequence; the variable sequence will generally be at least about 60 nt and not more than about 600 nt, more usually not more than about 400 nt; where the sequence codes for a T-cell receptor variable region, the sequence will generally range from about 270 to 330 nt, more usually from about 285 to 312 nt;

"J" intends the joining region and will generally be from about 42 nt to about 60 nt, more usually from about 45 nt to 57 nt, and frequently about 48 to 54 nt, where the J region will be selected from a limited number of sequences associated with the joining region exons of the T-cell antigen receptor subunit;

"TM" intends the transmembrane integrator sequence which will be a hydrophobic sequence of from about 51 to 90 nt, more usually from about 84 to 96 nt;

"d" will be 0 or 1;

"Cy" intends the sequence extending from the membrane into the cytoplasm, which will normally be from about 12 to 30 nt, more usually from about 15 to 24 nt, particularly about 15 to 18 nt; and "e" is an integer from 0 to 1.

Each of the two subunits, α- and β-, may be expressed independently in different hosts or in the same host. Where the two subunits are expressed in the same host, depending upon whether a microorganism host or mammalian host is employed will affect the processing of the subunits and assembling of the subunits into the T-cell receptor. Involved with processing is folding, glycosylation, transport through the endoplasmic reticulum and Golgi apparatus, cleavage with removal of the secretory leader sequence, as well as capping or blocking of the N-terminus by acetylation. As part of the processing or independent of the processing folding of the subunits and assembling of the subunits into the T-cell receptor must occur. With mammalian cells, it is to be expected that the resulting protein will substantially conform with the naturally occurring T-cell receptor in its chemical, physical and biological properties. However, with lower eukaryotes and prokaryotes, various of the process steps may occur in whole or in part, differently or not at all. Therefore, the sequences may be modified by replacing the wild type secretory leader sequence with a secretory leader sequence recognized by the expression host or provide for an initiation codon at the beginning of the variable region. The subunits may then be isolated in the cytoplasm and the receptor formed by bringing the α- and β-subunits together under renaturing conditions.

DNA coding for receptor subunit fragments should encode for a polypeptide of at least 8 amino acids, usually at least 15 amino acids (24 nt and 45 nt, respectively), so as to provide polypeptides having biological activity, e.g., immunological.

The constructions, as indicated, can be prepared by inserting DNA coding for only a portion of a T-cell antigen receptor subunit where the vector has one or more appropriate restriction sites, or can be modified, for example, by adapters, to provide for insertion at an appropriate site in relation to a promoter and associated regulatory sequence, e.g., RNA polymerase binding site for transcription and to appropriate translational regulatory sequences, e.g., ribosomal binding site, or to be in reading frame with a leader sequence.

The domains or regions of the T-cell antigen receptor can be employed individually or in combination. By employing cDNA, one can obtain the gene in open reading frame coding for the preprotein, that is the protein prior to processing, such as removal of the secretory leader, glycosylation, or the like. By restriction mapping the cDNA, one can determine the presence of convenient restriction sites adjacent the borders between the individual domains as indicated in the above formula. Where a restriction site is not at the border, one can still cleave at a site near the border, using either partial or complete digestion as appropriate with the appropriate restriction enzyme. Where nucleotides have been removed so as to have a truncated sequence, one may replace the nucleotide(s) employing appropriate adapters which allow for joining the domain of interest to another nucleotide sequence in proper reading frame. Where extra nucleotides are present, one can remove these by resection, e.g., employing Bal31, by primer repair, or the like. Alternatively, where there is degeneracy in the codon for a particular amino acid, in vitro mutagenesis may be employed to modify one or more nucleotides which would then provide the proper recognition sequence for a restriction enzyme. These techniques have been extensively described in the literature and do not require exemplification here.

The DNA sequences which are employed, may be the same or different from the sequences isolated in accordance with the subject invention. By employing the J or C domain sequences either by themselves or in combination with other sequences, e.g., transmembrane sequences, the subject sequences can be used as probes for determining the presence of homologous sequences in the same or different species and for isolating sequences having equivalent functions. In this manner, a repertory of sequences can be obtained which can be joined together to provide for a variety of cistrons coding for T-cell antigen receptors or hybrid proteins employing varying combinations of fragments from T-cell antigen receptors.

By joining the secretory leader sequence of the T-cell antigen receptors to a non-wild DNA sequence, one can provide for secretion of a hybrid protein into the nutrient medium and processing, so as to obtain a mature protein product from a mammalian host. Where the protein is a eukaryotic protein, it can be properly processed, so as to provide a product which is the same or substantially the same as the naturally-occurring eukaryotic protein. Alternatively, if one wishes to provide for specific proteins on the T-cell surface or surface of a different mammalian cell, one can interpose the foreign sequence coding for the foreign protein between the secretory leader sequence and the transmembrane sequence in place of the sequences coding for the variable, J and constant regions of the T-cell antigen receptor subunit. In this way, one can provide for a totally different surface membrane protein at the cell surface, modifying the surface characteristics of the cell.

By using the expression products of the subject constructs, one can obtain antibodies to the expression products, which can then be used for detecting the presence of T-cell antigen receptors or individual subunits, due to sharing idiotypic determinants or common determinants to the J or C regions.

The cloned DNA sequences, particularly of the sequences extending from the 5'-end of the C region to the 3'-end of the cytoplasmic region can be used as probes. Usually, the probes will be at least about 15 nt, more usually at least about 30 nt and will generally not exceed 1500 nt, more usually not exceeding about 1000 nt, preferably not exceeding about 500 nt of homologous sequence. Additional, non-homologous flanking sequences may be present which may be up to 5 knt or more.

The nucleotide sequences employed as probes may be RNA or DNA and may be labeled in a wide variety of ways. Commonly, probes are labeled with $^{32}P$ and may be detected by autoradiography. Alternatively, biotin, novel sugars, or any other molecule may be included by virtue of the use of synthetic techniques for producing the oligonucleotide. Thus, any terminal group may be introduced in a simple manner to act as a source of a detectable signal. These groups may be introduced directly or indirectly, that is, by covalent bonding, ligand-receptor bonding, e.g., haptens and antibodies, or the like. Illustrative labels which provide for a detectable signal include fluorescers, chemiluminescers, enzymes, radioactive labels, magnetic particles, and the like.

Two different methods for obtaining rare messenger RNA were employed for isolating the rare messenger RNAs associated with the T-cell antigen receptor subunits. The method employed for the β-subunit involved the separation of membrane-bound polysomal RNA from non-membrane-bound RNA. The membrane-bound polysomal fraction of RNA was then reverse transcribed to produce single-stranded (ss) cDNA. The cDNA was then labeled with $^{32}P$ and repeatedly hybridized with B-cell mRNA and fractionated on hydroxyapatite. Remaining ss cDNA which passed through the column was isolated. A second T-helper hybridoma was then used to prepare a cDNA library and was screened with the cDNA probes prepared from the first T-helper hybridoma. This resulted in substantial enrichment for T-cell-specific membrane associated sequences (about 200-fold).

The reduced number of selected clones was re-screened using the initially prepared probes. The positive clones were then nick-translated and hybridized to B-cell mRNA under Northern blotting conditions. Those clones that did not hybridize to the B-cell mRNA's were selected as T-cell-specific.

The clones were then employed to investigate somatic rearrangements as follows. Those which hybridize to RNAs having greater than 1000 nt were hybridized to Southern blots of genomic DNA from various sources including a helper T-cell hybridoma and a thymoma. The DNAs were prepared by standard methods, digested with a particular restriction enzyme, in this case, PvuII, electrophoresed through 0.9% agarose and blotted on to nitrocellulose. Moderate to strict stringency was employed, and both the thymoma and hybridoma were found to give substantially different patterns from the other non-T-cell DNA.

The method employed for the α-subunit involved a variable-region specific subtracted cDNA probe between T-cells of differing specificities. Random-primed labeled cDNA from the mRNA of a helper hybridoma was synthesized. After fragmentation to an average size of about 300-400 nt, sequences were subtracted with mRNA from at least two different T-helper hybridoma or T-helper like lymphoma line, using hydroxyapatite to separate single from double-stranded nucleic acid. The single-stranded cDNA remaining was then hybridized to a cDNA library prepared from the cell line providing the original cDNA. Further elimination of irrelevant sequences can be achieved by rescreening the positive clones with oligo-dT primed cDNA from the same T-helper hybridoma, where the cDNA is reverse transcribed from membrane bound polysomal mRNA subtracted with mRNA from a macrophage or other lymphocytic line. Resulting hybridizing clones are found to be related to the variable region of the T-cell receptor.

By employing hybrid DNA technology the α- and β-subunits can be prepared individually or combined as a receptor having high specificity and affinity for specific conformations of organic molecules, such as polypeptides, polysaccharides, lipids, haptens and combinations thereof. A class of receptors is provided analogous to the immunoglobulins which can be used in substantially the same way, but lacking properties associated with immunoglobulins, such as Fc determinants, complement associated cytotoxicity, or other characteristics specifically associated with immunoglobulins. The subject receptors can be used to compete with surface membrane bound T-cell receptors in vivo in blood to inhibit proliferation of helper cells activated by the homologous antigen.

The T-cell receptors may be used in most of the situations where immunoglobulins find use, such as diagnostic assays, affinity chromatography, site-directed therapy or diagnosis where the T-cell receptor may be conjugated directly or indirectly to radionuclides, nmr active compounds, fluorescers, toxins, e.g., abrin, ricin, etc., or the like.

By having the genes available for the α- and β-chains, the chains and, therefore, the receptors may be prepared in large amounts from cells other than human cells, which are less fastidious in their growth requirements than human cells. The T-cell receptos may be prepared in bacteria, e.g., E. coli, B. subtilis, etc., eukaryotes, e.g., yeast, filamentous fungus, murine cells, etc.

The following examples are offered by way of illustration and not by way of limitation:

EXPERIMENTAL

The procedure for gene isolation of genes encoding for helper T-cell antigen-specific receptor subunits α- and β- ($T_H$-Ag receptor, α- or β-subunit) is as follows.

The isolation of the β-subunit will be considered first. Membrane-bound T-helper cell cDNA probes was subtracted with B-cell messenger RNA and used to screen a cDNA library which was the product of another $T_H$-B-cell lymphoma combination. The library was constructed as described below for a B-cell-specific library (Davis et al., Proc. Natl. Acad. Sci. USA (in press)) and by a similar procedure for xenopus embryonal stage specific library (Sargent and Dawid, Science (1983) 222:135-139) using $T_H$-hybridomas M12 or 2B4 (Hedrick et al., Cell (1982) 30:141-152). The B-cell mRNA was obtained from the B-cell lymphomas L10A and Ba117 (Kim et al., J. Immunol. (1979) 122:549-554). The cDNA was $^{32}$P-labeled for detection. The $T_H$-B library was 20-fold enriched for T-cell-specific sequences as judged by the fact that 95% of the mass of the cDNA was removed in the subtraction at the hydroxyapatite stage.

(The exemplary procedure for the B-cell library follows. The cell lines Ba117, B-cell lymphoma (IgM-+IgD+Ia+) (Kim et al., J. Immunol. (1979) 122:549-554) and Bal4, T-cell thymoma (Thy1+Lyt1--Lyt2+TL+) (Kim et al., ibid. (1978) 121:339-344) were grown in RPMI, glutamine, 70% fetal calf serum and $5\times10^{-5}$M β-mercaptoethanol in a 5% $CO_2$ atmosphere. After growing to a high density ($1-2\times10^{-6}$/ml) refreshed with new media for 2 to 4 hr, the cells were chilled with PBS and harvested. The cells were washed several times in cold PBS, resuspended in 0.14M KCl, 0.02M Tris, pH 8.0, 0.0015M $MgCl_2$, lysed with the addition of NP-40 to 1% and the nuclei pelleted. The cytoplasmic fraction was made 0.5% SDS, 5 mM EDTA and extracted 2-3× with saturated precipitated with ethanol (Mushinski et al., Proc. Natl. Acad. Sci. USA (1980) 77:7405-7409) and the polyA+RNA selected on oligo-dT cellulose (1-2 passages).

cDNA from the B-cell lymphoma was synthesized from 1 to 5 μg template polyA+RNA in 50 mM Tris, pH 8.3, 6 mM $MgCl_2$, 70 mM KCl, 1 mM each dNTP, $^{32}$P-dCTP to give first strand specificity of $10^5$ cpm/μg), 10 μg/ml oligo-dT, 20 mM dithiothreitol, 100 μg/ml Actinomycin "D" in a 100 μl reaction mixture. Ten units AMV reverse transcriptase was added per μg polyA+RNA and incubated for 2 hr at 42° C. After adding an equal volume of 0.2M NaOH, the mixture was incubated at 70° C. for 20 min, cooled on ice, neutralized with 1M HCl and sodium acetate (pH 6.5) and SDS added to 0.2M and 0.1%, respectively. At room temperature, the cDNA was excluded from G-50F Sephadex in a Pasteur pipette column with a running buffer of 100 mM NaCl, 50 mM Tris, pH 7.5, 1 mM EDTA and 0.02% SDS. Fifty μg of tRNA was added as carrier and the cDNA precipitated in a silanized Eppendorf tube (1.5 ml). The precipitate was washed once with 70% ethanol, dried and resuspended in 0.5M phosphate buffer, 5 mM EDTA, 0.1% SDS and hybridized in sealed glass capillaries with the T-cell thymoma RNA at a 10-fold excess at 1 to 1.5 mg/ml. To absorb repetitive sequences, sheared mouse genomic DNA (1.2 mg/ml, 10 μg per reaction) was included. After boiling for 60sec, the mixture was incubated for 16 to 20 hr at 60° C. Hydroxyapatite chromatography was then used to fractionate the material in 0.12M phosphate buffer, 0.1% SDS, 60° C.

The single-stranded fraction was made double-stranded with DNA polymerase I (Klenow fragment), trimmed with S1 nuclease and G-C tailed into the PstI site of pBR322. The plasmids were then cloned into E.

coli at high efficiency (50–400×10³ μg/insert) with an average insert size about 500 nt.)

The library of 5000 selected clones was screened and rescreened by standard procedures (Maniatis et al. in *Molecular Cloning*, Cold Spring Harbor Press, Cold Spring Harbor, 1982) using the membrane-bound T-helper cell cDNA probes from the T-hybridoma 2B4 from which sequences common to B-cell messenger from the B-cell L10A had been subtracted (MBT$_{2B4}$-B$_{L10A}$). Thirty-five definite positives resulted, which was about 10% of the library. In order to determine which were derived from the same gene and which were different, as well as to remove only false positives, each of these plasmid clones was nick-translated and hybridized to representative Northern blots. Five were reactive with B-cell mRNA and the remaining 30 fell into one of the 10 distinct patterns of mRNA size and expression shown in the following Table.

TABLE

| Clone | Insert Size | Message Size | Expression Pattern* | | |
|---|---|---|---|---|---|
| | | | T-hy-bridoma | T-lym-phoma | B-lym-phoma |
| TM4 | 0.7 | 1.5,1.9, 4.5 kb | + | + | − |
| TM8 | 0.8 | 1.9 kb | + | + | − |
| TM26 | N.D. | 1.0 kb | + | N.D. | − |
| TM28 | 0.8 | 1.6 kb | + | + | − |
| TM29 | N.D. | 0.6 kb | + | − | − |
| TM30 | N.D. | 0.7 kb | + | + | − |
| TM33 | N.D. | 1.7,1.9, 3.0 kb | + | + | − |
| TM86 | 0.6 | 0.7 kb | + | + | − |
| TM90 | 0.25 | 1.7 kb | + | + | − |
| TM97 | 0.95 | 1.8,1.9 kb | + | + | − |

*T-hybridoma, 2B4 and C10; T-lymphoma, Bal4 and Bal13; B-lymphoma L10A and Bal17.

TM8 cross-hybridized strongly with a rat thy-1 cDNA clone. thy-1 is a classic T-cell membrane antigen.

A cDNA library was now prepared from the hybridoma 3.3T (Heber-Katz et al., supra).

Each of the seven clones which hybridized to messengers of at least 1000 nt were labeled and hybridized to genomic Southern blots composed of DNA from the thymoma BW5147 (from the mouse strain AKR, Heber-Katz et al., supra), AKR liver, the antigen-specific T-cell 2B4 (a fusion of T-cells from B10.A mice with BW5147), and B10.A liver. The DNAs were prepared by standard methods (Maniatis et al., supra), digested with a restriction enzyme PvuII, electrophoresed through 0.9% agarose and blotted on to nitrocellulose. The autoradiograms from the Southern blots showed that except for the restriction polymorphism between AKR and B10.A seen with TM8 (thy-1), the patterns of hybridization with each clone were identical for all of the sources of DNA except in the case of TM86. There was a strikingly different pattern of PvuII fragments that hybridized to the clone from either BW5147 or 2B4, as compared to liver DNA from either of the parental strains. The clones which were surveyed were also hybridized to EcoRI and HindIII digests of genomic DNA and in each case only TM86 showed a significant difference between the T-cell DNAs and liver DNAs. The TM86 clone is PstI excisable from pBR322.

To test whether genomic rearrangements of a receptor gene were unique for T-cells of different antigen specificities, genomic blots consisting of DNA from five antigen-specific T-cell hybridomas were hybridized with a nick-translated insert from clone TM86. The results were that DNA from each of the antigen-specific T-cells yielded a unique pattern. Three different B-cell lymphoma tumor DNAs gave patterns identical to that of the liver indicating that the rearrangement appeared to be unique to the T-cells.

Also a series of cytotoxic lines express messenger RNAs similar to those of T helper cells (by cross-reaction with the gene described here) and also display rearrangement of their genomic DNA.

In order to obtain other cDNA clones which arose independently in different T-lymphocytes, a thymocyte cDNA library was prepared using the lambda vector gt10 (generally available from Ronald Davis, Stanford University, Stanford, Calif.). The library was screened with the TM86 clone using standard conditions (Maniatis et al. in *Molecular Cloning* (Cold Spring Harbor Press) Cold Spring Harbor, N.Y. (1982)). The library was constructed from total thymocyte polyA+RNA from young, Balb/C strain mice. The cDNA was prepared using AMV reverse transcriptase (Amersham). The cDNA was not methylated, accounting for cleavage within the mRNA sequence on the 3′-side. After filling in with DNA polymerase I, EcoRI linkers were joined to each end. The resulting fragments were then fractionated in the desired size range, and inserted into the single EcoRI restriction site located in the phage repressor gene of the lambda vector gt10. Introduction of a DNA fragment into the repressor gene produces cI−phage, which forms a clear plaque. The cI+phage forms a turbid plaque, allowing for selection of hybrid phage. To eliminate the parent phage from the gt10 libraries, the bacterial host utilized was C$_{600}$rk−mk+hfI, on which the parent phage forms plaques at very low efficiency. The cI+parent phage is suppressed, while the cI−hybrid phage plates normally.

Positively hybridizing recombinants were subcloned into the EcoRI site of pUC9 (Viera and Messing, *Gene* (1982) 19:259–268). Three thymus-derived clones were obtained designated 86T1, 86T3 and 86T5. A partial restriction map is shown in FIG. 1. The 86T series molecules all end at the same 3′ position because of an internal EcoRI recognition site proximal to the 3′ end of the coding sequence. The 5′ end variation is presumably due to random chain termination during library construction.

Figure 2:
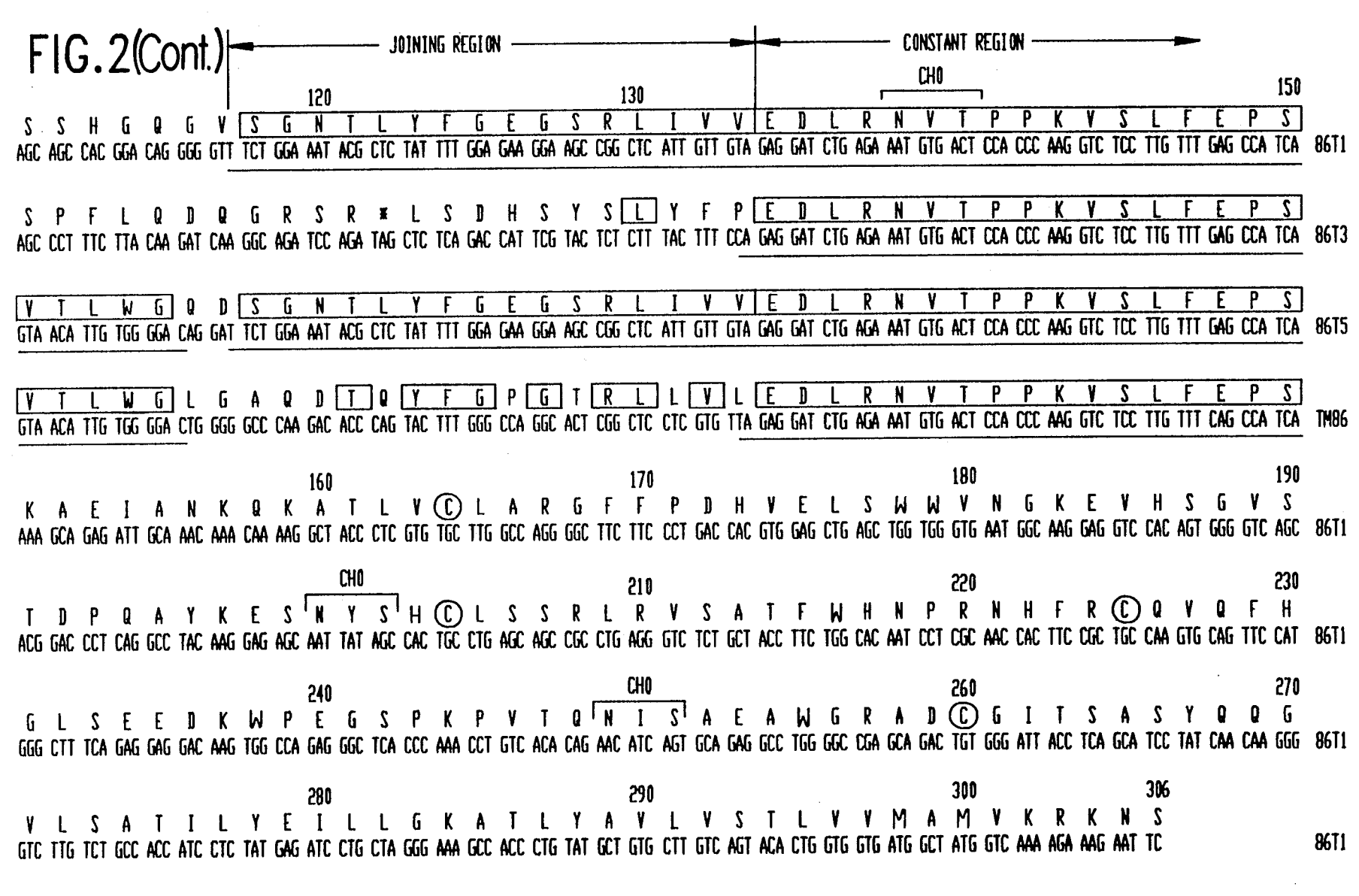

Based on the fact that the largest mRNA seen in Northern blots is 1300 nt, subtracting a polyA tail of 150–250 nucleotides gives an expected clone size of 1050–1150 nt. Therefore, it may be concluded that the 938 nucleotide size of 86T1 should contain most of the coding region sequence for a thymocyte molecule. 86T1 was completely sequenced and compared with the partial sequences of the other clones as shown in FIG. 2.

Based on the comparisons a number of conclusions may be derived: (1) No two 5′ ends are alike among the four cDNA clones, yet all have identical 3′ ends, except as noted in FIG. 1. The entire constant region of 86T3 was sequenced and was found to be identical except for one nucleotide with that shown for 86T1. This 5′ variable and 3′ constant region structure is analogous to immunoglobulin cDNA clones. (2) There is a stretch of hydrophobic amino acids immediately following the methionine initiation codon corresponding to the expected leader polypeptide. In particular, the sequence Leu-Leu-Leu is common among kappa light chain leader polypeptides. (3) A 16 amino acid element between the variable and constant regions is shared at the nucleotide level between 86T1 and 86T5, but not with 86T3 or TM86, suggesting an independently assorting J-like region. (4) Placement of cysteine and other residues suggests significant structural similarity to immunoglobulins and related molecules. (5) The apparent variable region of 86T3 appears non-functional because of the many (five) stop codons in frame with the otherwise normal constant region and, in fact, this clone has stop codons in reading frame, indicating that not all transcripts of this gene are successful in producing a viable molecule, at least in the thymus.

In order to analyze the sequence of this cDNA clone for evolutionary relationships with known proteins, the derived amino acid sequence was compared to the Dayhoff protein sequence data bank using the rapid comparison programs of Wilbur and Lipman, *Proc. Natl. Acad. Sci. USA* (1983) 80:726–730. From the Dayhoff bank of approximately 2300 sequences, the homologies of 25 sequences were greater than or equal to five standard deviations from the mean homology of the data bank. Of these 25 sequences, 24 were immunoglobulin constant or variable region sequences and one was a Class II human histocompatibility molecule. Furthermore, matches in the variable portion of 86T1 are with variable regions of immunoglobulins while those in the constant portion are with constant regions of immunoglobulin. Of 18 invariant residues in mouse kappa variable regions (Kabat et al., supra), 13 are present in the sequence of 86T1 and of the ten invariant residues of the heavy chain variable regions, six are present in 86T1. The spacing between the cysteine residues which form the disulfide loops of immunoglobulin variable regions is typically 65 amino acids for both kappa and lambda light chains and 70 amino acids for those of the heavy chains. The distance between the outermost two cysteines of the 86T1 variable region is an intermediate 68 amino acids. The alignment of the different immunoglobulin V regions predicts that the leader peptide of 86T1 will be cleaved just before the asparagine at position 20.

Pronounced homology was observed to immunoglobulins throughout what is probably the first constant region domain, particularly around the cysteine at position 164. In this region it was interesting to note that the sequence immediately 5' to the cysteine is homologous to light chains and the sequence 3' to heavy chains. Substantial homology is also observed to both kappa and lambda light chains around the last cysteine (position 260) in the 86T1 sequence.

Of the four clones, 16 amino acids are shared between the 86T1 and 86T5, but not with the other two clones sequenced, 86T3 and TM86. This homology falls precisely into the region occupied by joining (J) region elements in immunoglobulins. The putative J region of both 86T1 and TM86 show substantial homologies with all the immunoglobulin J regions. In terms of size, the putative J regions are more related to heavy chains (which average 17 amino acids) than light chains (13 amino acids).

In addition to the J element, the adjacent 5' region between amino acids 103-115 has substantial homology between 86T5 and TM86. In particular the 17 nucleotide and nine nucleotide identities between these two cDNA clones suggest other possible "mini-gene" elements possibly analogous to the D region of heavy chain immunoglobulins. Alternatively, these homologies may represent some highly conserved areas of related variable region genes.

A hydropathicity plot (Kyte and Doolittle, *J. Mol. Biol.* (1982) 157:105–132) was performed and indicated that: The 86T1 molecule has the alternating hydrophobic-hydrophilic stretches characteristic of globular proteins; the predicted leader polypeptide occurs in a hydrophobic environment; a transmembrane spanning region is indicated at the end of the 86T1 sequence, followed by a string of positive charges (lys-arg-lys), characteristic of the cytoplasmic portion of a number of lymphocyte cell-surface markers.

In conclusion, the structure of 86T1 is that of a 19 amino acid leader polypeptide, a 98 amino acid variable region, a 16 amino acid J region and a single globular constant region domain followed by transmembrane and cytoplasmic portions. By analogy to immunoglobulins, the two outermost cysteines in each globular domain would be linked and the last cysteine at position 260 would be bound to the other chain of the receptor heterodimer.

It was further found that antisera raised against synthetic peptide fragments of 86T1 can significantly inhibit the antigen-dependent release of IL-2 by T-helper hybridomas. It is therefore concluded that the locus described above represents a type of immunoglobulin gene specifically rearranged and expressed in at least some subsets of T-lymphocytes and that it plays a role in the recognition of antigen by T-cells.

The isolation and characterization of the $T_H$-Ag receptor $\alpha$-unit will now be described. Procedures which have been described previously in isolating and characterizing the $\beta$-subunit will not be repeated.

Calf thymus DNA was used to synthesize random prime $^{32}$P-labeled cDNA by standard procedures (Maniatis et al., supra) from polyA+cytoplasmic 2B4 mRNA. The cDNA was initially 700 nt average length and was allowed to fragment by autoradiolysis to about 300–400 nt in length over a two week period. Subtractive hybridization was then carried out employing hybridization and hydroxyapatite selection with $T_H$ hybridoma C10 mRNA, followed by the mRNA from the $T_H$-like lymphoma cell line EL-4. The twice subtracted probe was then hybridized to a filter of 2B4 cDNA library in the vector $\lambda$gt10. Approximately 20,000 plaques were screened. Seven positives were picked and rescreened with a probe of oligo-dT-primed cDNA made of membrane bound polysomal mRNA from 2B4, subtracted with mRNA from the P388D1 macrophage line (MBT*$_H$-Mac) Three of the seven positives were positive with the MBT*$_H$-Mac probe and two of these three cross-hybridized with each other. One of the cross-hybridizing probes was designated TT11 and chosen for further study. The TT11 cDNA clone was labeled by nick-translation and hybridized to a Northern blot containing a panel of mRNAs as follows: a) Bal17, B-cell lymphoma; b) M104e plasmacytoma; c) 3T3, fibroblast line; d) P338D1, macrophage line; e) 2B4; f) EL-4; g) BW5147. All are polyA+cytoplasmic RNAs prepared by standard procedures. A single band was observed at about 1.8 kb for 2B4, while two bands were observed for EL-4, a weaker band at 1.8 kb and a second band at 1.3 kb in the EL-4 lane.

To demonstrate that the gene encoding for the sequence of TT11 was as a result of a rearrangement, genomic DNAs from the livers of different mouse strains, various T-cell lines and hybrids of the B-cell lymphoma L10A were digested with a) HindIII; b)

Figures 3A, 3B:
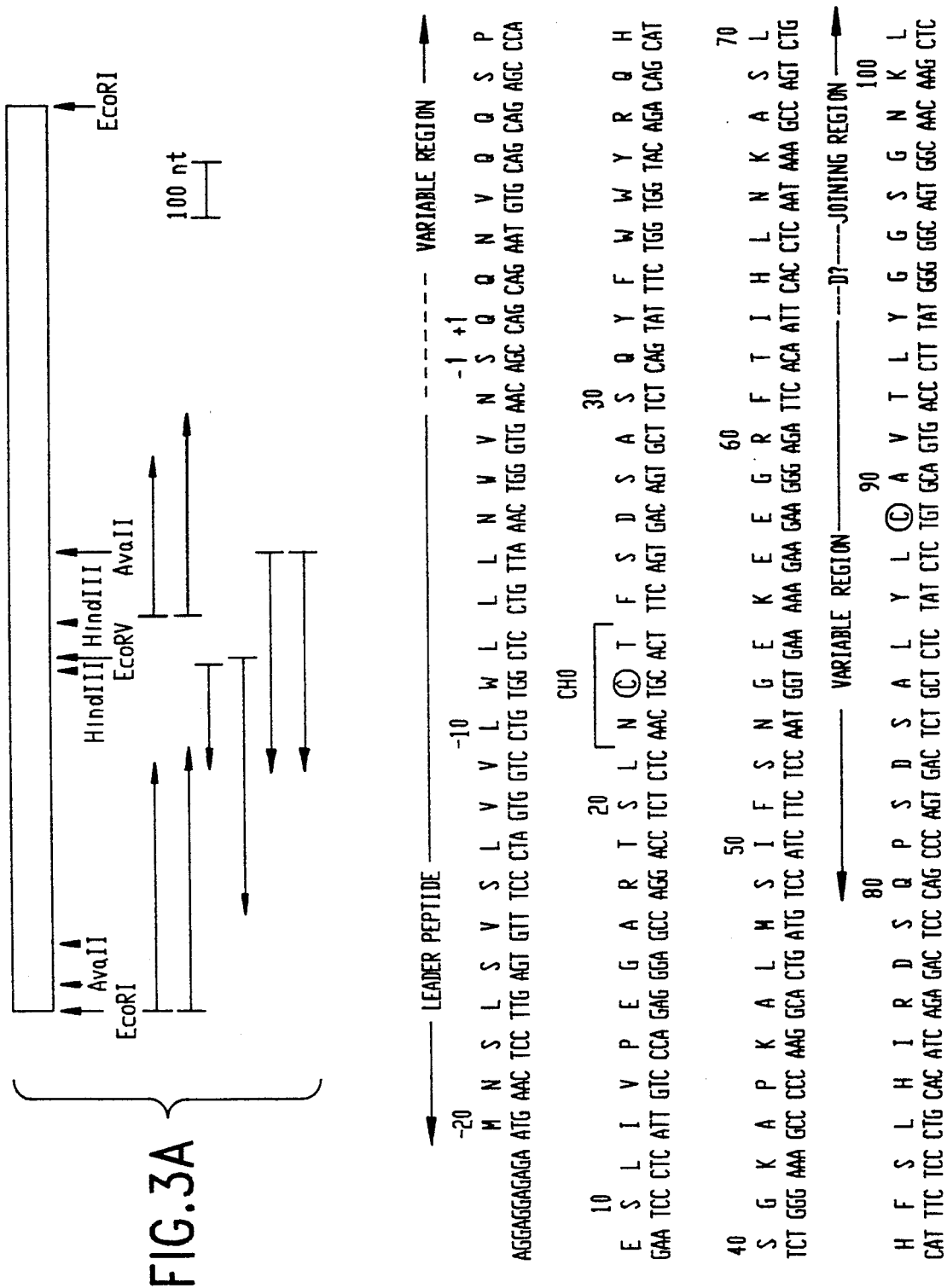
FIG. 3A shows the sequencing strategy of TT11 cDNA clones, with thin lines indicating 5'-end labeling with polynucleotide kinase and thick lines indicating 3'-end labeling with the Klenow fragment of DNA polymerase I.
FIG. 3B also shows the nucleotide sequence, predicted amino acids, and indicates generally the individual regions. "CHO" indicates potential signal sequences for N-linked glycosylation.

EcoRV; c) XbaI; d) BglII and electrophoresed through 0.7% agarose, blotted on nitrocellulose and hybridized by standard methods to a probe from the 5' half of TT11 (EcoRI-EcoRV, FIG. 3A). Two of the lanes designated FN1 and FN13 were from KLH reactive $T_H$ hybridomas derived from BALB/c×C57B/6 strain mice and the AKR strain thymoma line BW5147. A new band appears in a HindIII digest of FN1 with respect to parental DNAs, while one band in an EcoRV digest of AKR liver DNA disappears in BW5147 and an EcoRI digest shows a new band appearing in BW5147 versus the parental liver DNA. Two bands are observed which are polymorphic for an XbaI digest of C57B/6 DNA. Both of these bands are present in the FN1 hybrid, but only one occurs in FN13, which could only be the result of a rearrangement or partial deletion of the chromosome. A new band in FN1 versus the parentals is observed in a BglII digest. Although no one digest shows evidence of rearrangement in all T-cell DNAs, there are enough indications of such events to believe that TT11 is a T-cell receptor-like gene.

The TT11 cDNA clone was partially sequenced by the procedure of Maxam and Gilbert, *Meth. Enzym.* (1980) 65:499–560, utilizing the strategies shown in FIG. 3A and the sequences shown in FIG. 3B. The clone was oriented by a polyA stretch (about 150 nt) at the 3'-end and sequencing of the 5' half revealed a long open reading frame of 810 nt, with an initiation codon (ATG) within the first 12 nt. This sequence has regions similar to the Ig leader, variable region, joining (J) region, and constant region, just as do the T-cell receptor β-chain and the HDS4 gene clone of Saito et al., *Nature* (1984) 309:757–762.

Features of the sequence are an extra cysteine outside of the putative intra-domain cysteines in the constant region (common to the latter two T-cell specific genes), followed by a transmembrane region and a cytoplasmic region, all of which are encoded as separate exons in the β-chain genes. There are four potential N-linked glycosylation sites, similar to the four or five found in different β-chain sequences. It would appear that only three of these four potential sites are available for glycosylation since the most carboxy terminal one is embedded in the transmembrane region.

The exact position of processing of the T-cell receptor α-subunit has not been established, but by analogy to immunoglobulin types, it would be just before the glutamine at +1 shown in FIG. 3B. Alternatively, based on the N-terminal amino acid sequence of the human β-chain from the REX T-cell line (Acuto et al., *Proc. Natl. Acad. Sci. USA* (1984) 81:3851–3855) the processing point would be just before the asparagine at +3. In the first place, the molecular weight would be 27 kd, which agrees with the molecular weight observed by Allison et al., who obtained a molecular weight of 27kd from a murine α-chain stripped of N-linked sugars with endo F.

The overall homology with the V and C regions of Ig counterparts is relatively low (10–26%). However, many of the conserved residues found in all the five known Ig-like genes are present, particularly in the V region and the J region elements. The spacing of the cysteines in the TT11 variable region is 65 amino acids, which is identical to that of the light chains, and the sequence "WYRQ" starting at residue 35 and "DSA-Y-CAV" at residues 83–91 are also highly conserved in most I-, G- and T-cell receptor V regions. As with the β-chain and HDS4, the J region in the most highly conserved portion, with 7/16 residues homologous to the β-chain concensus sequence (Gascoigne et al., *Nature* (1984) 310:387–891) and 9/16 the same as $J_T3$, (Gascoigne et al., supra). TT11 has the sequence "ILLLK" in the transmembrane region, characteristic of T-cell receptor sequences, where the conservation of a charged amino acid (lysine or arginine) in a transmembrane is unusual and not found in other members of the immunoglobulin super family.

While not established, there appears to be strong support that there is a D region present in the α-subunit. In particular, just 5' to the "SGN" amino acid sequence of the J region (which marks the 5' border of $J_T3$ in the β gene complex), there is a nucleotide sequence "GGGGG". This is characteristic of gene D regions of the β-subunit, where 7 out of 14 contain runs of between 3–7 Gs on their 3' side (Tonegawa, *Nature* (1983) 302:575–581). The Northern blot data described previously further support the presence of a D region. The two bands clearly visible in the EL-4 lane, and observed in other $T_H$ lines, is characteristic of the DJC transcript of the β-chain which is 300 nt shorter than the VDJC transcript (Kavaler et al., *Nature* (1984) 310:421–423).

To establish the ratio of the mRNAs for the α- and β-subunits, thymocyte, conA (concanavilin A) stimulated spleen and 2B4 cDNA libraries were surveyed with TT11, HDS4 and $C_T\beta$ probes. Whereas TT11 and $C_T\beta$ are present in fairly similar frequencies, 1:1–1:3 in the 2B4 and conA spleen libraries, respectively, HDS4 is much rarer. A substantial change in ratio of TT11 to β-chain in immature versus mature T-cells was observed suggesting that TT11 gene expression may come after expression of β-chain, analogous to light chain immunoglobulin expression following that of the heavy chain in B-cells.

It is evident from the above results that novel DNA sequences and constructs are provided which provide for the expression of T-cell antigen receptors, subunits and fragments thereof. The DNA sequences can be used in a variety of ways to produce hybrid proteins, which may be retained as surface membrane proteins, can be labeled to provide for probes for determining lymphocyte origin or type, for isolating DNA sequences from T-cells, for use as primers for producing DNA sequences coding for the T-cell receptor subunits, or for use for secretion of foreign proteins from a mammalian host cell. The peptides can be used for the production of antibodies for isolation of T-cell antigen receptors, for removal of T-cells from cell mixtures, for identification of T-cells, or for binding to T-cells in vivo or in vitro, so as to affect their viability, proliferation, secretion of factors, or the like.

Although the foregoing invention has been described in some detail by way of illustration and example for purposes of clarity of understanding, it will be obvious that certain changes and modifications may be practiced within the scope of the appended claims.

What is claimed is:

1. A substantially purified nucleic acid polymer coding for at least a region of a mammalian T cell receptor β subunit, which region is selected from the group consisting of the constant region, the variable region, the joining region, the diversity region, the transmembrane region, and the cytoplasmic region, said nucleic acid polymer encoding less than a full length β subunit.

2. The nucleic acid polymer of claim 1 in which the region is in the constant region.

3. The nucleic acid polymer of claim 1 in which the region is in the variable region.

4. The nucleic acid polymer of claim 1 in which the region is in the joining region.

5. The nucleic acid polymer of claim 1 in which the region is in the diversity region.

6. The nucleic acid polymer of claim 1 in which the region is in the transmembrane region.

7. The nucleic acid polymer of claim 1 in which the region is in the cytoplasmic region.

8. The nucleic acid polymer of claim 1, in which the region of a mammalian T cell receptor $\beta$ subunit is a region of a murine T cell receptor $\beta$ subunit.

9. A substantially purified nucleic acid polymer comprising a nucleotide sequence as depicted in FIG. 2 encoding a region of a murine T cell receptor subunit selected from the group consisting of a variable region, a joining region, a constant region and a transmembrane region.

10. A substantially purified nucleic acid polymer encoding at least one region of a human mammalian T cell receptor $\beta$ subunit, which region is selected from the group consisting of the constant region, the variable region, the joining region, the diversity region, the transmembrane region, and the cytoplasmic region, said nucleic acid polymer encoding less than a full length $\beta$ subunit of a human T cell antigen receptor.

11. The nucleic acid polymer of claim 10 in which the region is the constant region.

12. The nucleic acid polymer of claim 10 in which the region is the variable region.

13. The nucleic acid polymer of claim 10 in which the region is the joining region.

14. The nucleic acid polymer of claim 10 in which the region is the diversity region.

15. The nucleic acid polymer of claim 10 in which the region is the transmembrane region.

16. The nucleic acid polymer of claim 10 in which the region is the cytoplasmic region.

17. A substantially purified nucleic acid construct comprising the nucleic acid polymer of claim 10.

18. A transformed host cell containing the nucleic acid of claim 10 or 17.

19. A substantially purified oligonucleotide encoding a fragment of a mammalian T cell receptor $\beta$ subunit, said oligonucleotide hybridizing selectively to one of the strands of a double stranded DNA molecule, one strand of which DNA molecule encodes the mammalian T cell receptor $\beta$ subunit.

20. The oligonucleotide of claim 19 which hybridizes to the DNA coding for the murine T cell receptor $\beta$ subunit.

21. A substantially purified oligonucleotide encoding a fragment of a human mammalian T cell receptor $\beta$ subunit, said oligonucleotide being at least twelve nucleotides in length and encoding less than a full length $\beta$ subunit of a human T cell antigen receptor, said oligonucleotide hybridizing selectively to one of the strands of a double stranded DNA molecule, one strand of which DNA molecule encodes the human mammalian T cell receptor $\beta$ subunit.

22. A substantially purified heterologous nucleic acid construct comprising the oligonucleotide of claim 21.

23. A transformed host cell containing the oligonucleotide of claim 21.

24. A substantially purified nucleic acid construct coding for at least a region of a mammalian T cell receptor $\beta$ subunit, which region is selected from the group consisting of the constant region, the variable region, the joining region, the diversity region, the transmembrane region, and the cytoplasmic region, said region encoding less than a full length $\beta0$ subunit of the mammalian T cell receptor $\beta$ subunit.

25. The construct of claim 24 in which the region is the constant region.

26. The construct of claim 24 in which the region is the variable region.

27. The construct of claim 24 in which the region is the joining region.

28. The construct of claim 24 in which the region is the diversity region.

29. The construct of claim 24 in which the region is the transmembrane region.

30. The construct of claim 24 in which the region is the cytoplasmic region.

31. A method of obtaining a nucleic acid polymer encoding a mammalian T cell receptor $\beta$ subunit comprising the steps of:
   (a) contacting a sample containing nucleic acids which encode mammalian T cell proteins under hybridization conditions with the nucleic acid polymer of claim 2, or at least twelve contiguous nucleotides thereof, as a probe; and
   (b) isolating a nucleic acid polymer (1) which is selectively hybridizable to such probe and (2) which demonstrates T cell specific gene rearrangements.

32. A method of obtaining a polynucleotide encoding a fragment of a mammalian T cell receptor $\beta$ subunit comprising the steps of claim 31 and further comprising the steps of:
   (c) amplifying the nucleic acid polymer of step (b) to produce a duplex nucleic acid;
   (d) sequencing at least one strand of the duplex of step (c); and
   (e) isolating a polynucleotide of the nucleic acid polymer of step (c), which polynucleotide encodes a fragment of a mammalian T cell receptor $\beta$ subunit.

33. A method of obtaining a nucleic acid polymer encoding a mammalian T cell receptor $\beta$ subunit comprising the steps of:
   (a) contacting a sample containing nucleic acids which encode mammalian T cell proteins under hybridization conditions with a polynucleotide encoding the constant region as depicted in FIG. 2, or at least twelve contiguous nucleotides thereof;
   (b) isolating the nucleic acid polymer hybridized to such polynucleotide or oligonucleotide, which nucleic acid polymer demonstrates T cell specific gene rearrangements.

34. A method of obtaining a polynucleotide encoding a fragment of a mammalian T cell receptor $\beta$ subunit comprising the steps of claim 33 and further comprising the steps of:
   (c) amplifying the nucleic acid polymer of step (b) to produce a duplex nucleic acid;
   (d) sequencing at least one strand of the duplex of step (c); and
   (e) isolating a polynucleotide of the nucleic acid polymer of step (c), which polynucleotide encodes a fragment of a mammalian T cell receptor $\beta$ subunit.

35. A method of obtaining a nucleic acid polymer encoding a mammalian T cell receptor $\beta$ subunit comprising the steps of:
   (a) containing T cell specific nucleic acid polymer with B-cell specific nucleic acid polymer under hybridization conditions;

(b) amplifying the non-hybridized T cell specific nucleic acid polymer;

(c) isolating the amplified non-hybridized T cell specific nucleic acid polymer which demonstrates T cell specific gene rearrangement.

36. An isolated transformed host cell containing the construct encoding the mammalian T cell receptor $\beta$ subunit of claim 24, 25, 26, 27, 28, 29, or 30.

37. A substantially purified heterologous nucleic acid construct encoding a fragment of a mammalian T cell receptor $\beta$ subunit in which the nucleic acid construct comprises a first polynucleotide coding for a fragment of a mammalian T cell receptor $\beta$ subunit, said fragment being at least twelve nucleotides in length and less than a full length $\beta$ subunit, said first polynucleotide being operatively linked to and controlled by a second polynucleotide, which second polynucleotide regulates gene expression in a cell.

38. An isolated host cell containing a heterologous nucleic acid construct encoding a fragment of a mammalian T cell receptor $\beta$ subunit in which the nucleic acid construct comprises a first polynucleotide coding for at least a fragment of a mammalian T cell receptor $\beta$ subunit, said fragment being at least twelve nucleotides in length; said first polynucleotide which is operatively linked to and controlled by a second polynucleotide, which second polynucleotide regulates gene expression in the cell so that the cell produces a protein which is the fragment of the mammalian T cell receptor $\beta$ subunit, said fragment being less than the full length $\beta$ subunit.

39. The cell of claim 38 in which the fragment encodes a constant region.

40. The cell of claim 38 in which the fragment encodes a variable region.

41. The cell of claim 38 in which the fragment encodes a joining region.

42. The cell of claim 38 in which the fragment encodes a diversity region.

43. The cell of claim 38 in which the fragment encodes a transmembrane region.

44. The cell of claim 38 in which the fragment encodes a cytoplasmic region.

45. The cell of claim 38 in which the region is a hybrid combination of one or more regions selected from the group consisting of a constant region, a variable region, a joining region, a diversity region, a transmembrane region, and a cytoplasmic region.

46. A process for producing a selected fragment of the T cell receptor $\beta$ subunit, comprising the steps of:
    (a) culturing the host cell of claim 38 so that the cultured cells produce a fragment of the T cell receptor subunit; and
    (b) recovering the fragment of the T cell receptor subunit so produced, which fragment is less than the full length $\beta$ subunit.

47. A substantially purified RNA which encodes a fragment of a T cell receptor $\beta$ subunit when said RNA is translated by ribosomes, which fragment is less than the full length $\beta$ subunit.

* * * * *

UNITED STATES PATENT AND TRADEMARK OFFICE
CERTIFICATE OF CORRECTION

PATENT NO.    :    5,316,925

DATED         :    May 31, 1994

INVENTOR(S)   :    Mark M. Davis and Stephen M. Hedrick

It is certified that error appears in the above-identified patent and that said Letters Patent is hereby corrected as shown below:

Please add --Assignee: Board of Trustees of Leland Stanford Junior University, Stanford, Calif.--.

In Column 18, Claim 24, line 4, replace "$\beta$0" with --$\beta$--.

In Column 18, Claim 35, line 66, replace "containing" with --contacting--.

Signed and Sealed this

Twenty-third Day of December, 1997

Attest:

BRUCE LEHMAN

Attesting Officer

Commissioner of Patents and Trademarks